United States Patent [19]

Iwasaki et al.

[11] 4,184,919

[45] Jan. 22, 1980

[54] METHOD OF GELLING MICROBIAL MYCELIA

[75] Inventors: Taisuke Iwasaki, Hino; Toshihiko Kikuchi, Tokyo, both of Japan

[73] Assignee: Snow Brand Milk Products Co., Ltd., Sapporo, Japan

[21] Appl. No.: 891,217

[22] Filed: Mar. 29, 1978

Related U.S. Application Data

[63] Continuation-in-part of Ser. No. 780,496, Mar. 23, 1977, abandoned.

[30] Foreign Application Priority Data

Mar. 31, 1976 [JP] Japan .................................. 51-35249

[51] Int. Cl.² ............................................. C07G 7/02
[52] U.S. Cl. ...................................... 435/175; 195/54; 195/56; 195/63; 195/DIG. 11; 435/182
[58] Field of Search ...................... 195/54, 56, 68, 63, 195/DIG. 11

[56] References Cited

U.S. PATENT DOCUMENTS 3,980,521  9/1976  Amotz et al. .......................... 195/68

FOREIGN PATENT DOCUMENTS 2223340  11/1972  Fed. Rep. of Germany.

OTHER PUBLICATIONS

Chibata et al., Applied Microbiology, May 1974, pp. 878–885.
Broun et al., Biotechnology and Bioengineering, vol. XV, pp. 350–375 (1973).

*Primary Examiner*—Lionel M. Shapiro
*Attorney, Agent, or Firm*—Stevens, Davis, Miller & Mosher

[57] ABSTRACT

The disclosed method involves adding a crosslinking reagent to mycelia which contain enzymes, freezing the mixture and then thawing the frozen mycelia. The resulting gelation immobilizes the intracellular enzyme in the mycelia. The gel may be used in the enzyme industry as a highly active enzyme preparation.

9 Claims, No Drawings

METHOD OF GELLING MICROBIAL MYCELIA

CROSS-REFERENCE TO RELATED APPLICATION

The present application is a continuation-in-part of application Ser. No. 780,496, filed Mar. 23, 1977, now abandoned and entitled "METHOD OF GELLING MICROBIAL CELLS".

FIELD OF THE INVENTION

This invention relates to a method of gelling microbial cells of microorganisms, in the form of mycelia, containing intracellular enzymes.

BACKGROUND OF THE INVENTION

With progress in enzyme-utilizing industries in recent years, various techniques have been proposed for immobilizing enzymes on water-insoluble supports to increase their utility. It would be desirable to immobilize enzymes, which have been utilized as water soluble catalysts, to keep the enzymes from free diffusion and efflux into the reaction substrate, thus enabling their recovery and reuse, as well as enabling continuous reaction by charging them into the columns. The techniques for immobilizing enzymes proposed so far include immobilization of an enzyme by the entrapment in a gelled, water-insoluble, high molecular weight substance (for example, polyacrylamide), coupling of the enzyme to a water-insoluble support (for example, porous glass) and the like. It is, however, difficult at present to put the above techniques into practical use, because their application to the immobilization of intracellular enzymes requires the steps of rupturing the microbial cells containing the enzymes and/or ultrasonic treatment, freeze-thaw grinding, organic solvent treatment, autolysis and the like to isolate the enzymes from the cells, which techniques present efficiency and process problems. More specifically, gelled cells prepared from ruptured cells or autolyzed cells are deficient in the mechanical strength required for using the cells as a column packing. In view of the foregoing, various methods have been proposed for the immobilization of intracellular enzymes including coupling of enzymatically active microbial cells to other protein-like substances and entrapment of such cells in the lattice of a high molecular substance. None of these prior art procedures, however, have proven satisfactory.

BRIEF SUMMARY OF THE INVENTION

It has now been discovered that the microbial cells of microorganisms in the form of mycelia can be converted into a three-dimensional sponge- or gel-like lattice structure by freezing a suspension of the microbial whole mycelia in a medium containing a reagent having a crosslinking capability, more specifically, a reagent having bifunctional groups, and thawing the frozen mass in an organic solvent or, alternatively, by freezing the above suspension after mixing with the above reagent and the organic solvent, thawing the frozen mass and, if required, subjecting to further drying. The gel is formed without rupturing the microbial mycelia, i.e., with essentially unruptured, intact mycelia. Thus, "whole mycelia" is meant to describe the mycelia as being essentially intact and unruptured.

Therefore, it is an object of this invention to provide an advantageous method of gelling microorganism mycelia containing intracellular enzymes.

Other objects of the invention will become apparent from the description which follows.

DETAILED DESCRIPTION OF THE INVENTION

A wide variety of microorganisms in the form of mycelia are suitable for use in the present invention so long as they possess intracellular enzymatic activity, but it is preferred that the microbial cells per se have a gelling capability. Since the gelling capability of the cells differ according to the type of microorganism and, even as between strains of the same species, it is preferable to select microorganisms of a strain having a high gelling capability. Where the highly gelable microbial cells have undesired intracellular enzymes, they are, preferably, used after inactivation of the undesired enzymes by a thermal or chemical treatment. On the other hand, where immobilized enzymes having several types of enzymatic activities are required, several kinds of microbial mycelia can be used in combination and immobilized by the method of this invention.

The degrees of gelation for various kinds of microorganisms are shown for reference in table 1 below:

Table 1

| Kind of Microorganisms | Degree of Gelation |
| --- | --- |
| Actinomycetes | ++ |
| Mould (Fungi) | ++ |
| Yeast | → |
| Bacteria | — |
| Lactobacillus | + |

— no gel formed
+ → ++ gel formed (weak → strong)

The degree of gelation in the table above is the result of gellation of the given type of microorganism by the method of this invention.

It can generally be observed, as seen from the above table, that the gelling capability is high in microorganisms in the form of mycelia such as Actinomycetes and mould, while extremely low for yeast and bacteria which do not form mycelia. It is surprising that the microorganisms in the form of mycelia show a high gelling capability without rupturing. In case that the raptured mycelia are used, on the other hand, the gelling capability formed in weakend.

In this invention, it is, of course, possible to use microorganisms containing in their mycelia various enzymes such as glucose-isomerase, β-galactosidase, invertase, protease and lipase.

In preparing a suspension of microbial mycelia, possessing an enzymatic activity, the microbial mycelia are separated and collected by way of a centrifugation, or another conventional separation technique, form a culture broth of the microorganism, washed with phosphate buffer or the like to remove culture medium components and then suspended in a phosphate buffer. By taking care to avoid rupture of the mycelia, little or not enzyme is lost by washing with the buffer. Where two or more kinds of microbial cells are used, suspensions of each type are prepared and then mixed together or, alternatively, a mixture of the microbial cells may be formed in a single suspension.

A reagent having a crosslinking capability is added to the suspension of the microbial cells prepared as above. Many reagents are suitable for this purpose and the crosslinking agent may be selected from among those conventionally employed for the immobilization of enzymes by crosslinking. Reagents having bifunctional groups are generally used. Reagents which are suitable for this purpose include, for example, glutaraldehyde, bis-diazobenzidine-2,2'-disulfonic acid, 1,5-difluoro-2,4-dinitrobenzene, epichlorohydrin, phenol.disulfonyl-chloride, xylene-diisocyanate, toluene-diisocyanate, 2-amino-4,6-dichloro-S-triazine, 2,4,6-5-richloro-S-triazine and the like. The amount of the reagent added to the suspension of the microbial mycelia is selected in accordance with the species and strain of microorganisms, the type of intracellular enzyme and, in particular, the gel forming capability of the microorganism.

A test was conducted to determine the relationship between the concentration of glutaraldehyde used and the degree of gelation of the microbial mycelia where the glutaraldehyde was added to a suspension of Streptomyces sp. and the results are shown in table 2 below. This test was carried out in the following manner.

Streptomyces sp. possessing glucose.isomerase activity was incubated while shaking for two days at 30° C. on a medium containing xylose as a carbon source. Then, the culture broth obtained was subjected to centrifugal separation to separate and collect the microbial cells, which were repeatedly washed with M/100 phosphate buffer (pH 7.0) until the adhering culture medium was substantially removed. 5 g by wet weight of the microbial cells thus obtained was suspended in 60 ml of M/100 phosphate buffer (pH 7.0). To the suspension, was added a 25% glutaraldehyde solution in different amounts to give the various concentrations shown in table 2. Then, after freezing them in a freezer over night, the frozen microbial cells were thawed in acetone and air-dried to form gel-like cell coagulates, which were immersed in water to form sponge-like gelled cells. The degree of gelation for each sample was then evaluated.

Table 2

| Glutaraldehyde concentration (%) | Degree of Gelation |
| --- | --- |
| Control | − |
| 0.0025 | + |
| 0.0125 | + |
| 0.025 | + + |
| 0.05 | + + |
| 0.075 | + + |
| 0.1 | + + |
| 0.125 | + + |

− no gel formed
+ → + + gel formed (weak → strong)

As can be seen from the table above, preferred degrees of gelation can be attained with the addition of 0.025–0.1% by volume glutaraldehyde. In the addition of glutaraldehyde, no affect was observed on the activity of intracellular glucose-isomerase.

Then, after the cell suspension to which the above reagent had been added was placed in a freezer and frozen over one night or so, the frozen cells were thawed in an organic solvent to form a sponge-like gel and then air dried to form gel-like cell coagulates. Gellation occurs only after freezing and thawing. That is, the gellation does not occur by the addition of glutaraldehyde to the suspension of cells. Immersion of the dried gel-like cell coagulates into water reproduced a sponge-like gel of a shape corresponding to the shape in the frozen state. Accordingly, by freezing the above cell suspension into the shape such as a cylinder, disc, plate or cube, gelled cells are obtainable in a fixed shape.

Any organic solvent may be optionally used as the thawing medium so long as it does not adversely affect enzymatic activity. Acetone, methanol, ethanol and the like are preferably used. The presence of the solvent in the thawing environment serves to prevent autolysis and rupture of the mycelia with attendant loss of enzymes to the thawing medium.

It is also possible in this invention to obtain gelled microbial mycelia by adding the reagent to the suspension of the microbial mycelia to first immobilize the mycelia, adding the aforementioned organic solvent and then freezing and thawing the mixture in water, instead of using the organic solvent as the medium for the thawing of the mycelia. In this alternative process, microbial mycelia gelled by the addition of the organic solvent to the mycelia suspension prepared as above (or by the addition of the suspension to the organic solvent) are subjected to centrifugal separation or other separation techniques to remove excess organic solvent. Then, the above reagent was added and mixed with the wet mycelia thus obtained and thereafter frozen and then thawed in water. While the gelled mycelia thus prepared can be directly utilized as an immobilized intracellular enzyme, they can also be used after further drying under a low temperature, for example, by freeze-drying.

As described above, by processing the enzymatically active microbial mycelia in the combined treatments with the crosslinking reagent, organic solution and freezing according to this invention, not only the intracellular enzymes are immobilized but also the mycelia are interconnected in a three-dimensional network to form a sponge-like configuration thereby immobilizing the intracellular enzymes supported on the cells per se. Since the gelled mycelia obtained according to the invention have a sponge-like, three-dimensional configuration therethrough, the gelled mycelia can be advantageously used as a column packing. Moreover, since the gelled mycelia can optionally be kept in a shape corresponding to that of their frozen state, immobilized intracellular enzymes suited to the column packing procedure for continuous reaction can be provided with industrial advantages.

EXAMPLE 1

Streptomyces sp. isolated from soil and having a glucose-isomerase activity was inoculated into a liquid medium (pH 7.0) containing 3% wheat bran, 2% corn steep liquor and 0.024% $CoCl_2.6H_2O$, and cultured with shaking at 30° C. for 24 hours. Therafter, the microbial mycelia were separated and collected and then subjected to repeated centrifugal washing with M/100 phosphate buffer at pH 7.0. to remove the culture medium components. 5 g by wet weight of the washed microbial mycelia was suspended in 60 ml phosphate buffer at pH 7.0, to which 0.2 ml glutaraldehyde (as 25% aqueous solution) was added and thoroughly mixed by stirring. Then they were frozen in a freezer over night. The coagulated mycelia were thawed in an acetone solution and the gelled mycelia thus formed were air dried on a filter paper. The gelled cells showed a glucose-isomerase activity of 0.34 unit/mg.

One "unit" as used herein refers to the amount of enzyme capable of producing 1 mg fructose after reaction for one hour at 70° C. in a 0.1 M glucose solution (containing 0.05 M phosphate buffer at pH 7.2 and 0.01 M MgSO$_4$.7H$_2$O).

EXAMPLE 2

The frozen microbial mycelia of *Streptomyces albus* (produced by Godo Shusei Co.) were thawed and then subjected to centrifugal washing with M/100 phosphate buffer at pH 7.0 until the culture medium components were completely removed. Then, 5 g by wet weight of the mycelia thus obtained were gelled in the same manner as described in Example 1. Then, the gelled product thus obtained was packed into a column (1.5×5.5 cm), through which 1 M glucose solution containing 0.005 M MgSO$_4$ (dissolved in M/50 phosphate buffer pH 7.0) was passed at 70° C. with a space velocity (SV) of 1.2. The conversion rate to fructose was 35%.

What is claimed is:

1. A method for gelling enzyme-containing microbial mycelia comprising:
    forming a liquid suspension of whole mycelia;
    adding a crosslinking agent to the suspension;
    freezing the suspension; and
    thawing the frozen suspension in an organic solvent or water to thereby form a sponge-like gel of the whole mycelia.

2. The method as claimed in claim 1, wherein said microbial mycelia have a gelling capacity.
3. The method as claimed in claim 1, wherein said suspension of the microbial mycelia is prepared by separating and collecting microbial mycelia from a culture medium and suspending them in a buffer solution.
4. The method as claimed in claim 1, wherein said suspension of the microbial mycelia is a mixed suspension containing microbial mycelia of a high gelling capability and microbial mycelia of a low gelling capability.
5. The method as claimed in claim 1, wherein said crosslinking agent has bifunctional groups.
6. The method as claimed in claim 5, wherein said crosslinking agent is glutaraldehyde.
7. The method as claimed in claim 1, wherein said organic solvent is acetone, methanol or ethanol.
8. The method as claimed in claim 1, wherein said frozen mycelia are freeze-dried.
9. A method for gelling enzyme-containing microbial mycelia comprising:
    forming a liquid suspension of the whole mycelia;
    adding an organic solvent and a crosslinking agent to the suspension;
    freezing the suspension; and
    thawing the frozen suspension to thereby form a sponge-like gel of the mycelia.

* * * * *